United States Patent [19]

Blass et al.

[11] Patent Number: 5,356,807

[45] Date of Patent: Oct. 18, 1994

[54] CULTURED CELL LINE OF ADULT DIPLOID CELLS FROM HUMAN BRAIN AND MENINGEAL TISSUE

[75] Inventors: John P. Blass, Bronxville; Ronald S. Black, Ossining, both of N.Y.

[73] Assignee: Cornell Research Foundation, Ithaca, N.Y.

[21] Appl. No.: 940,926

[22] Filed: Sep. 8, 1992

[51] Int. Cl.[5] ................................................ C12N 5/00
[52] U.S. Cl. .............................. 435/240.2; 435/240.21
[58] Field of Search ............. 435/240.2, 240.3, 240.31, 435/240.21, 1

[56] References Cited

PUBLICATIONS

DeGiorgio et al, J. Cell. Biology, 115 (3 Part 2) p. 214A (1991).
Norton et al., Glia, 1 (6), pp. 403–414 (1988).
Blass et al., Soc. Neurosci. Abstr., 17 (1–2) p. 552 (1991).
Black et al, J. Neurological Sciences, 111 (1), pp. 104–112 (1992).
Blass et al., Neurobiol. Aging, 11 (3), p. 332 (1990).

*Primary Examiner*—Irene Marx
*Assistant Examiner*—Susan M. Dadio
*Attorney, Agent, or Firm*—Yahwak & Associates

[57] ABSTRACT

A culture medium, a technique for the culture of adult diploid cells from brain and meningeal tissue, explanted diploid cells from brain tissue having neuronal antigenic markers, and the use of cultured diploid cells from brain tissue having neuronal antigenic markers for the screening of neuroactive compounds are disclosed.

5 Claims, No Drawings

CULTURED CELL LINE OF ADULT DIPLOID CELLS FROM HUMAN BRAIN AND MENINGEAL TISSUE

Partial funding for the making of the invention described herein was obtained from the National Institute of Aging. Accordingly, the federal government has certain rights to this invention under 35 USC ∫ 200 et seq.

It is estimated that ten percent of persons older than 65 years have mild to severe dementia. Alzheimer's disease is the most common cause of chronic dementia with approximately two million people in the United States having the disease. Although once considered a condition of middle age, it is now known that the histopathologic lesions of Alzheimer's disease (i.e., neuritic amyloid plaques, neurofibrillary degeneration, and granulovascular neuronal degeneration) are also found in the brains of elderly people with dementia. The number of such lesions correlates with the degree of intellectual deterioration. This high prevalence, combined with the rate of growth of the elderly segment of the population, make dementia one of the most important current public health problems.

The etiology and pathogenesis of Alzheimer's disease are not known. Cytoarchitectural studies of the cerebral cortex have shown that neurofibrillary changes occur in neurons within specific cortical laminae, especially in the temporal lobe and in the hippocampus. Neurochemical studies of the cerebral cortex have shown a relatively specific reduction in choline acetyltransferase, the enzyme required for synthesis of the neuro-transmitter acetylcholine (ACh). The degree of reduction of ACh correlates with the severity of dementia, and may reflect loss of neurons in the substantial innominata of the basal forebrain that form the cholinergic projection to the hippocampus and cerebral cortex.

The need for effective treatments for Alzheimer's disease is widely recognized. Research on the therapeutic approaches to this disease currently focus on attendant neurotransmitter deficits. However, treatments at the neurotransmitter level are not expected to halt the progression of neuronal degeneration and death. The few therapeutic trials with agents designed to treat cellular defects in Alzheimer's cells have not yielded dramatic results. There is, therefore, a continuing need to screen for medications that may ameliorate the underlying cellular defects.

Accordingly, one aspect of the present invention is to describe a cell culture medium which will support the continuous passage of cells having typical neuronal markers, obtained from brain tissue, through a number of serial passages.

Another aspect of the present invention is to describe a chemically defined brain tissue culture medium (RBM) which includes, in combination, Dulbecco's Modified Eagle Medium (DMEM, Gibco); nerve growth factor (NGF) at a concentration of from about 0.1 $\mu$g/ml to about 1 $\mu$g/ml; fibroblast growth factor (FGF) from about 5 ng/ml to about 50 ng/ml; insulin from about 10 $\mu$g/ml to about 50 $\mu$g/ml; transferrin from about 50 $\mu$g/ml to about 150 $\mu$g/ml; progesterone (about 20 nM), putrescine (about 100 $\mu$M); sodium selenite (about 30 nM); and antibiotics such as penicillin (about 25 units/ml), streptomycin (about 25 $\mu$g/ml) and amphotericin B (about 6.3 $\mu$g/ml ). The RBM was supplemented with 20% FCS (Gibco) unless otherwise indicated. The specific ranges of concentration given above are not critical to the medium according to the present invention, and concentrations may be varied without untoward effects to the cultured cells.

Although concentrations may vary, we have found that a preferred culture medium (preferred because of cost, ease of manufacture and support of cell growth for cells having typical neuronal markers in accordance with the present invention)is one containing DMEM; 0.1 $\mu$g/ml of NGF (7S form, Collaborative Research); 10 ng/ml of FGF (Collabortive Research); insulin (25 $\mu$g/ml), transferrin (100 $\mu$g/ml), progesterone (20 nM), putrescine (100 $\mu$M), and sodium selenite (30 nM); and penicillin (25 units/ml), streptomycin (25 $\mu$g/ml) and amphotericin B (6.3 $\mu$g/ml ). The medium was routinely supplemented with 20% FCS (Gibco) unless otherwise indicated.

It is also an aspect of the present invention to describe a procedure by which cells demonstrating neuronal rather than astroglial markers can be cultured from adult human brain and meninges.

It is still a further aspect of the present invention to describe an in vitro paradigm for cellular studies of adult human brain.

These and other aspects of the present invention will become more apparent to the reader after consideration of the following examples and detailed description of the invention.

The following disclosure, examples and tables are thus provided to allow one to receive a more complete understanding of the present invention. These examples are not intended nor provided to limit the scope of the present invention in any manner, and it would be improper for one to interpret them as doing so.

Until recently, the culture of cells with neuronal properties has depended upon either explantation of nonreplicating cells from fetal or neonatal brain, or on the use of sxtablished cell lines from neuroblastoma or other neurogenic tumors. Recently a line has been described from a child with megalancephaly, a rare and potentially fatal disorder in which neurons continue to proliferate into postnatal life [see Science 248:603 (1990)]. Also, limited growth of possible neuronal precursor cells in culture has been claimed from adult mouse striatum [see Science 255:1707 (1992)]. Thus, it has not previously been reported in the scientific literature that serial culture of diploid cells having an array of typical adult neuronal markers and taken from mammalian brain cortex or meninges, including human cortex or meninges, was possible.

The present invention is a major advance over previous reports in that it describes culture media and other techniques which allow for (1) the serial passage in culture of normal diploid cells with neuronal markers (at least 38 passages over two years for the rat cells and at least 15 passages over 18 months for the human cells); (2) the culture of cells which contain an array of adult neuronal markers from normal human as well as normal rodent cerebral tissues; (3) the culture of cells which express neuronal markers from meningeal samples as well as from samples of brain; and (4) the culture of cells which express neuronal markers from normal human autopsy as well as biopsy tissues.

The following example is provided to show the culture media and technique which made the serial culture of diploid cells containing typical neuronal markers and taken from mammalian brain cortex or meninges possible.

EXAMPLE I

Cerebral cortices were collected and pooled aseptically from three 60 day old Wistar rats. The specimen was stripped of meninges, cut and minced into 8 mm³ cubes, and placed in culture flasks (Corning Glass Works) that had been precoated with poly-L-lysine (50 µg/ml, MW 150–300 kDa, Sigma). The culture medium (RBM) necessary for the successful serial culture of diploid cells according to the present invention is a modification of that reported by Bottenstein [see Adv. Cell Neurobiol. 4:333 (1983)], supplemented with fetal calf serum and growth factors. RBM contained Dulbecco's Modified Eagle Medium (DMEM, Bibco); nerve growth factor (NGF, 0.1 µg/ml, 7S form, Collaborative Research); fibroblast growth factor (FGF, 10 ng/ml, Collabortive Research); insulin (25 µg/ml), transferrin (100 µg/ml), progesterone (20 nM), putrescine (100 µM), and sodium selenite (30 nM); and penicillin (25 units/ml), streptomycin (25 µg/ml) and amphotericin B (6.3 µg/ml ). The RBM was supplemented with 20% FCS (Gibco) unless otherwise indicated.

Cells growing in this medium grew slowly, and the medium was changed once weekly before the first passage and twice weekly subsequently. When the medium was changed, only half was removed and replaced, on the assumption that the "conditioned" medium left in the flask would contain uncharacterized and perhaps as yet unknown growth factors produced by the cells. This technique proved reproducible as it yielded cultures on three separate trials, using three rats each trial, over a period of several months. Although not critical to the present invention, this partial replacement of media is a preferred requirement for best results utilizing the technique according to the present invention. The specific amounts of nutrients contained in the RBM used in this experiment are not critical and may vary within scientifically acceptable limits from those given. However, the presence of NGF and FGF are necessary for the culture medium according to the present invention.

The technique described in Example I was successfully used in separate trials using cells from rat brain. The culture medium described in Example I also allowed the propagation of similar cells to be grown from human autopsy and biopsy brain and meningeal tissue as described below.

The most extensive studies conducted from cells cultured utilizing this technique have been done with cells derived from the third attempt with rat brain. Thus, "RB3A" cells are one example of diploid cells according to the present invention, and these cells are described in greater detail below.

The RB3A cells grow briskly after 37 passages in culture, with a doubling time of approximately 2 days. The cultures have been restarted successfully from samples frozen (in 10% dimethylsulfoxide, at a cell concentration of 1.5 ×10⁶/ml). Flow cytometry and karyotyping indicate that the cells are diploid. Furthermore, there was no evidence of malignancy in the animals from which the brain tissue was obtained, nor in the other animals or humans from which similar lines have been obtained. The cells have been cloned, and studies suggest that the properties of the clones are similar to those of the parent cells.

The following Table 1 presents the results of immunocytochemical and immunoblotting analysis of RB3A cells grown in RBM containing 20% FCS.

TABLE I (Constituents of RB3A Cells)

| Antigen | Antibody | Antibody type | Immunocytochemistry (dilution) | Immunoblotting (dilution) |
|---|---|---|---|---|
| Neurofilament (heavy) | NE 14 | mAb | +(1:100) | +(1:10) |
| Neurofilament (heavy) | N 52 | mAb | +(1:100) | ND |
| Neurofilament (heavy) | R2B3 | mAb | +(1:100) | ND |
| Neurofilament (heavy) | 200 EL | pAb | +(1:5000) | +(1:500) |
| Neurofilament (medium) | NN 18 | mAb | +(1:100) | +(1:10) |
| Neurofilament (medium) | Hyacinth | pAb | +(1:5000) | +(1:500) |
| Neurofilament (light) | NR 4 | mAb | ±(1:100) | −(1:10) |
| Neurofilament (light) | 70C | pAb | ±(1:5000) | −(1:1000) |
| Neurofilament (light) | NF-L-N | pAb | ±(1:5000) | −(1:500) |
| Peripherin | | pAb | ND | −(1:1000) |
| NF-66 | | pAb | ND | −(1:500) |
| Neurone-Specific Enolase | | pAb | +(1:5000) | +(1:500) |
| tau | tau-1 | mAb | ND | +(1:500) |
| tau | tau-2 | mAb | +(1:1000) | ND |
| Synaptophysin | SVP-38 | pAb | +(1:5000) | ND |
| Synapsin | | pAb | −(1:5000) | −(1:500) |
| Tyrosine Hydroxylase | 20/40/15 | mAb | +(1:100) | ±(1:25) |
| Tyrosine Hydroxylase | | mAb | +(1:100) | ±(1:25) |
| Tyrosine Hydroxylase | | pAb | +(1:5000) | +(1:3000) |
| Tyrosine | | pAb | +(1:5000) | ND |
| Choline acetyltransferase | 11-255 | mAb | −(1:5) | ND |
| Glutamate Decarboxylase | | pAb | +(1:5000) | ND |
| GABA | | pAb | ±(1:5000) | NA |
| Serotonin | | pAb | −(1:5000) | NA |
| Met-enkephalin | | pAb | +(1:5000) | ND |
| Neurotensin | | pAb | +(1:5000) | ND |
| Somatostatin | | pAb | ±(1:5000) | ND |
| Neuropeptide Y | | pAb | ±(1:5000) | ND |
| Substance P | | pAb | −(1:5000) | ND |
| GFAP | GA5 | mAb | −(1:100) | −(1:200) |
| Myelin Basic Protein | | mAb | −(1:100) | −(1:100) |
| S-100 | | pAb | atypical (nuclear; 1:5000) | −(1:500) |
| Galactocerebroside | | pAb | atypical (diffuse cytoplasmic) | NA |
| Vimetin | V9 | mAb | +(1:1000) | +(1:200) |
| Desmin | DE-B-5 | mAb | −(1:100) | −(1:10) |
| Poly virus | | mAb | −(1:100) | ND |

In this table, the antigens are named without abbreviations; mAb=monoclonal antibody; pAb=polyclonal antibody; +=definite reactivity; ±=probable reactivity; − −=no significant activity compared to a simultaneous control (irrelevant antibody or non-immune IgG); ND=not determined; NA=not applicable.

Neuronal markers present in RB3A cells included: the heavy (200 kDa) and medium (160 kDa) neurofilament subunits (NF-H & NF-M); "neuron-specific" enolase (NSE); tau proteins; synaptophysin; tyrosine hydroxylase (TH); glutamate decarboxylase and probably GABA; and the neuropeptides met-enkephalin and neurotensin, probably neuropeptide Y and somatostatin, but not substance P. Although immunocytochemistry suggested the presence of the light (70 kDa) neurofilament subunit, immunoblots were not confirmatory, nor did immunoblots indicate the presence of the neurofilaments peripherin and NF-66. Evidence was not found for the presence of synapsin, cholineacetyltransferase, or serotonin.

Glial cell markers in these cultured cells were not present as determined by immunoblotting or by immunochemistry. Neither glial fibrillary acidic protein (GFAP) nor myelin basic protein (MBP) were found by either technique. Immunoreactivity for S100 protein was not found on immunoblots, and was largely nuclear on immunocytochemistry. Immunocytochemical reactivity with an antiserum to galactocerebrol side was in a diffuse cytoplasmic pattern rather than the membrane staining expected for this galactolipid, and the specificity of the staining with this antiserum remains uncertain.

The provenance of the RB3A cells remains unclear, although it appears unlikely that mature neurons dedifferentiated and replicated. A possibility is that RB3A cells are originally glial cells which express certain neuronal marker proteins under the culture conditions used; glial cells cultured in the medium described in Example I may have expressed neuronal marker proteins. Another possibility is that a small population of precursor cells which are pluripotential or are relatively early in a neuronal lineage persist even into the adult brain and can proliferate given the proper cultural conditions. Yet another possiblity is that the cells which were cultured from samples of brain were derived from the layer of meninges (pia) which is closely adherent to cortex. These cells are believed to be of neuroectodermal origin, and therefore to have had the potential to differentiate into neurons.

Conventional clinical and experimental experience indicates that new neurons are not formed at a significant rate in injured mammalian brain. However, if cells which can differentiate in a neuronal direction in tissue culture are present in adult mammalian brain and/or meninges, then these cells, i.e., the cells cultured in accordance with the present invention, may provide a treatment for brain trauma; for neural transplantation, endogenous cells are an attractive alternative :to endogenous nonneural (e.g. adrenal medullary) or foreign neural tissues. Methods by which cells cultured in the manner described according to the present invention could find use in neurotherapy would be in the treatment of a variety of neurodegenerative diseases and in brain injury through transplantation. For example, in the case of brain injury, a small amount of meningeal tissue or brain tissue from the injured patient (or from a donor) could be removed without causing any further neurologic deficit from a "silent" area of the cerebral cortex, such as the nondominant temporal lobe. Cells would be cultured according to the methods described and would be grown in the laboratory until sufficient cells were available for transplantation. The cultured cells could be stereotaxically reintroduced into the area of the brain which had been injured and their growth might help in the functional recovery of the injured area. In the case of neurodegenerative diseases, the cells could be reintroduced into the area of the brain affected by the degenerative process (such as the caudate nucleus in Huntington's disease, or the substantial nigra or striatum in Parkinson's disease).

Diploid cells from normal rat brain that replicate in culture and synthesize a number of neuronal "marker" proteins should also provide useful tools for studying neuronal differentiation. The RB3A cells react immunocytochemically with antibodies to several, but not all, neurotransmitters and neurotransmitter marker enzymes (see Table 1). Accordingly, further studies using the neurotransmitter marker tyrosine hydroxylase (TH) produced by the RB3A cells have been performed. In these cells, the immunocytochemical reactivity for all the neurotransmitters found involved effectively all of the cells in the culture, albeit to varying degrees. The surprising implication is that the same cells express, albeit perhaps at low levels, a number of different neurotransmitter markers. This interpretation is in accord with the belief that the RB3A cells are relatively undifferentiated precursor cells.

With this work with RB3A cells suggesting it would be possible to culture cells from the central nervous system tissues of adult animals which exhibit neuronal properties and express neuronal, but not glial, antigens, adult human central nervous system tissues were next studied.

Human cell cultures were obtained as part of a protocol for the use of neurosurgical waste tissue at Cornell University Medical Center. In all cases, tissue was removed to gain access to primary or metastatic brain tumors. Only tissue samples not involved with tumor on gross inspection was used. Cultured cells were obtained from seven of the nine samples studied.

The most detailed studies made in accordance with the present invention were conducted in cells obtained from the ninth sample (HB-9), which was from the left temporal lobe of a 45 year old man with a malignant glioma. The tumor was approximately 6×6 ×7 cm. The tissue sample was removed to gain access to the tumor, and was grossly free of involvement by tumor on dissection. Histological examination of the tumor indicated that it was a glioblastoma multiforme. Histologically, ganglion-like cells or other features of tumors of mixed phenotype were not present. On immunocytochemical staining, no reactivity was detected with any of the both monoclonal and polyclonal antibodies used in this study for neurofilament (NF-H, NF-M, and NF-L) subunits. A few areas of the tumor showed staining for neuron-specific enolase (NSE). Staining for glial fibrillary acidic protein (GFAP) was regionally heterogeneous, with many areas of the tumor showing strongly positive staining but some areas showing no GFAP staining.

EXAMPLE II

A tissue sample (approximately 2 gm) was obtained in a sterile fashion in the operating theater and transported to a tissue culture facility in the "biopsy medium" (BMd) described below, where it was minced in to 5–10 mm$^3$ pieces and placed into tissue culture flasks (Gibco) which had been precoated with polylysine (50 $\mu$g/ml, MW 150–300 kDa, Sigma). The BMd contained: Dulbecco's Modified Eagle Medium (DMEM, Gibco); nerve growth factor (NGF, 0.1 $\mu$g/ml, 7S form, Collaborative Research); fibroblast growth factor (bFGF, 10 ng/ml, Collaborative Research); components of the N2 medium described for the growth of neuronal cells in culture [see Adv. Cell Neurobiol. 4:333 (1983)], namely insulin 25 $\mu$g/ml, transferrin 100 $\mu$g/ml, progesterone 20nM, and sodium selenite 30 nM, all Sigma; and antibiotics, namely penicillin (25 units/ml), streptomycin (25 $\mu$g/ml) and amphotericin B (6.3 $\mu$g/ml), all Gibco. The BMd was also supplemented with 20% FCS (Gibco). Medium was changed twice weekly. Only half of the medium was replaced at each change, on the assumption that the "conditioned" medium would contain uncharacterized and perhaps yet unknown growth factors produced by the cells.

The cells were sensitive to trypsin, and were therefore subcultured either by gentle scraping of by light trypsinization. Routinely, trypsinization or scraping was stopped when about 75% of the cells had been removed from the surface, and the parent flask was used for reculture. These HB-9 cells have been subcultured eight times over 10 months, stored frozen using 10% dimethylsulfoxide at a cell concentration of $1.5 \times 10^6$/ml, and restarted from frozen samples.

Cultures of HB-9 cells consisted of relatively pleomorphic, flat polygonal cells with frequent long processes. This morphology appears stable, and consistent through a number of doublings of approximately 18 days.

The following example describes immunoblotting of HB-9 cells. Immunoblots were also performed on RB-3 cells. Results are in Table II which follows.

EXAMPLE III

HB-9 confluent T75 flasks were homogenized in lysate buffer (50 mM Tris pH 7.4, containing 1 mM PMSF, 1 mM EGTA, 50 µM leupeptin, and 0.04 U/ml aprotinin). An aliquot of homogenate was removed and Triton X-100 was added to the remaining homogenate to a final concentration of 1.0%. The Triton containing fraction was then centrifuged at 100,000×G for 30 minutes. The homogenate and particulate fractions were suspended in sample buffer containing 7M urea, 10 mM Na phosphate (pH 7.2), 2 mM EGTA, 0.5% 2-mercaptoethanol, 1 mM PMSF, 25 µM leupeptin, and 0.04 U/ml aprotinin. Protein concentration was determined by a dye binding method [see Anal. Biochem 72:248 (1976)]. Samples were treated in a boiling water bath for 10 min, and electrophoresed by SDS-PAGE [see Nature 227:680 (1970)]. Proteins were then electrotransferred to nitrocellulose membranes, and the nitrocelluose transfers were probed with the antibodies of interest (Table II), and immunoreactivity was visualized using the appropriate goat second antibodies conjugated with alkaline phosphatase (Bio-Rad) with 5-bromo-4-chloro-3-indolyl phosphate and nitro blue tetrazolium (both Sigma) as color developing reagents. Molecular weight markers were also electroblotted, and stained with amido black.

For studies of intermediate filaments, the triton insoluble pellet was analyzed. For detection of cytoskeletal antigens, rat spinal cord cytoskeleton [see J. Neurochem 39:1252 (1982)), was used as the immunoblotting standard. For studies of NSE and other soluble proteins, the homogenate fraction was analyzed, and a rat brain homogenate was used as the standard.

As depicted in the following Table II, immunoblotting according to Example II demonstrated the presence of the three main neurofilament subunits (NF-H, NF-M, and NF-L).

TABLE II

| (Constituents of HB-9 Cells) | | | |
|---|---|---|---|
| Antigen | Antibody | Immunocytochemistry | Immunoblotting |
| NF-H | pAb 200EL | + | + |
| NF-H | mAb N52 | + | − |
| NF-H | mAb NE14 | + | − |
| NF-M | mAb Hyacinth | + | + |
| NF-M | mAb BF-10 | + | + |
| NF-M | mAb NN-18 | + | + |
| NF-L | pAb 70C | + | + |
| NF-L | pAb NFL-N | + | + |
| NF-L | mAb NR4 | + | + |
| NF-66 | pAb | − | − |
| Peripherin | pAb | − | − |
| GFAP | mAb GA5 | ± | − |
| Vimentin | mAb V9 | + | + |
| Desmin | mAb DEB5 | − | − |
| NSE | pAb | + | + |
| Synapsin | pAb | − | − |
| Synaptophysin | mAb SVP38 | − | − |

As depicted in Table II, the presence of NF-L was confirmed by immunoblotting with both a polyclonal antibody to the purified rat protein and with a polyclonal antibody raised to the N-terminal sequence of rat NF-L. NF-M was demonstrated on immunoblot with both polyclonal and monoclonal antibodies. NF-H was demonstrated by immunoblotting with a polyclonal antibody raised against bovine NF-H, although not with two monoclonal raised against bovine NF-H, although not with two monoclonal antibodies which had been raised to rat rather than to human NF-H. No evidence was found for the presence of peripherin nor of the 66 kDa intermediate filament protein NF-66 (which appears to be identical with α-internexin). Vimentin was present, and could be detected in as little as one microgram of cytoskeletal preparation. NSE, another typical neuronal marker, was also present in the HB-9 cells. GFAP was not detected on immunoblots.

EXAMPLE IV

For immunocytochemical staining, cells were plated onto chamber slides (Nunc Inc.) which had been precoated with polylysine (as described in Example II). After sufficient growth had occurred, the cells were rinsed and fixed with freshly prepared 4% paraformaldehyde in TBS (50 mM Tris 150 mM NaCl, pH 7.4) for 30 min. Endogenous peroxidase activity was quenched with 0.3% hydrogen peroxide in ice-cold methanol. For cytoskeletal antigens, cells were permeabilized with 0.1% Triton-X100 for 10 minutes. After rinsing, cells were blocked with 5% bovine serum albumin (crystalline grade)in TBS for two hours and incubated with primary antibodies overnight. After rinsing, cells were developed by the avidin-biotin complex technique, using biotinylated secondary antibodies and streptavidin, with Vector Elite kit (Vector Labs). Incubation with primary antibody was routinely overnight. Color was developed using 0.05% diaminobenzidine and 0.01% hydrogen peroxide in 0.1M Tris buffer, pH 7.2. Absorption controls for neurofilament staining was performed by adding 0.4 mg/ml of the rat spinal cord preparation which had been dialyzed against 50 mM Tris, 150 mM NaCl buffer.

Immunocytochemistry confirmed the presence of the three neurofilament subunits (NF-L, NF-M, NF-H), with redundant antibodies for each subunit. The pattern of NF staining was cytoskeletal. Immunocytochemical reactivity to NSE was also found in the HB-9 cells, in a diffuse cytoplasmic pattern. Vimentin staining, in a cytoskeletal pattern, was observed; vimentin is found in immature neurons in vivo, as well as in a variety of cultured cells in vitro. Immunoreactivity to peripherin, NF-66, and desmin was not found. Peripherin and NF66 are typically associated with cells from the peripheral nervous system and desrain with mesodermal cells. Immunocytochemical reactivity for GFAP was not present.

EXAMPLE V

Flow cytometry was performed on a sample of cells according to the following protocol. Cells were stained with the DNA specific fluorochrome 4,6-diamino-2-phenyl indole (DAPI; Polysciences) [see Cancer Res. 44:83 (1984)]. Normal peripheral blood human and rat lymphocytes served as the DNA ploidy standard. The fluorescence of individual cells was measured with an ICP-22 flow cytometer (Ortho Diagnostics), using a UG-1 excitation filter and a combination of the dichroic mirrors and emission filters to transmit the blue-green emission spectrum of DAPI at 590+20 nm. The data was stored and analyzed using the Phoenix Flow Systems ™ software.

Flow Cytometry of the HB-9 cells after six passages and eight months in culture demonstrated that approximately 52% of the cells were diploid and approximately 48% tetraploid. The slow growth of the HB-9 cells precluded effective karyotyping, despite numerous attempts.

These experimental findings indicate that human brain cells cultured according to the present invention expressed the three most unique markers of adult neurons, namely the neuronal intermediate filament proteins NF-H, NF-M, and NF-L. They also contained NSE, a widely used marker of neurons in mixed cultures of neural origin; NSE has also been found in some tumors of nonneural origin. A straightforward explanation of these results is that the HB-9 cells are the human analogues of the "neuronal" cells described above from adult rat cortex.

It seems less likely that the HB-9 cells were derived from astroglia, since they showed no characteristics of glia; astroglia cultured from adult human brain characteristically contain GFAP, which was absent from the HB-9 cells, and never contain neurofilaments, which were present in the HB-9 cells.

It also seems relatively unlikely that the HB-9 cells were derived from the tumor in this patient. It is, of course, impossible to rule out the possibility that some cells from the glioblastoma multiforme infiltrated the apparently normal tissue removed to gain access to the tumor and used for culturing the cells. However, the neurofilaments NF-H, NF-M, and NF-L were found in all the HB-9 cells and not in the tumor, and GFAP was found in the tumor but not in the HB-9 cells.

The HB-9 cells did not show the polyploidy expected of a highly malignant glioblastoma multiforme. Repeated attempts to karyotype the HB-9 cells in early passages were unsuccessful, due to the paucity of metaphase plates obtained in these very slowly dividing cells. Flow cytometry after the cells had been in culture for 8 months showed diploid and tetraploid cells but not polyploidy; tetraploidy can occur in cultures of normal tissue, particularly as cultures approach senescence. The HB-9 cultures did not have the appearance of malignant cells in culture, and showed marked contact inhibition.

The potential use of cultured cells from adult human central nervous tissue which express neuronal properties is readily apparent [see Soc. Neurosci. Abstr. 17:553 (1991)]. The use of such cultured cells from adult human brain for transplantation and repair involves a series of assumptions about the plasticity of the adult human nervous system and its ability to form appropriate new connections and networks. The culture model for human central nervous tissue, such as for the HB-9 cells described herein, according to the present invention has, however, a more immediate use for studies of molecular and cellular aspects of diseases of the human nervous system. A number of properties of interest cannot be studied in neurons in autopsy human brain because of artifacts induced agonally and postmortem-for instance, signal transduction, labile mRNAs and proteins, and regulation of cellular function. These properties can readily be studied in tissue culture. Cultures from adult human brain are of particular interest in examining the mechanisms by which genetic diseases of the nervous system impair the function of nerve cells from patients with such disorders. These include the genetic forms of common diseases such as Alzheimer's disease. Such cultures may also provide another system for testing the effects of innovative medications for testing the cellular abnormalities in such disorders.

The methods according to the present invention have allowed the establishment of cell lines from autopsy and biopsy human brain and meninges, including from subjects with neurodegenerative disorders. By examinatior of these cells in culture, and comparison with cells cultured from control individuals, abnormalities specific to the disease in question can be elucidated. In addition to providing insight into the pathophysiology of the disorder, this will allow the cells to be used to screen large numbers of compounds for their possible effectiveness in the disorder. Compounds which are capable of ameliorating the disease specific abnormalities in the cell culture system may be most promising to test in animals and humans (which is far more costly and poses some risk to the patients). An analogous system, cultured fibroblasts, has been used to test treatments for Alzheimer's disease in this laboratory [Malow et al., Arch Neurol, 46:1201 (1989)]. Previous studies had shown isoproterenol-stimulated cyclic adenosine monophosphate (cAMP) production to be abnormal in the Alzheimer cells. A potential therapeutic agent in Alzheimer's disease, L-carnitine, was tested in the cell culture system and was found to reverse this abnormality in the cultured cells.

Fibroblast cell lines from ten patients with Alzheimer's disease, and ten age-and sex-matched control lines were tested. Growth medium was removed from the cells and, after rinsing, replaced with medium containing 10 $\mu$M isoproterenol with or without the addition of 0.6 nM L-carnitine. Cyclic AMP was measured by radioimmunoassay (Amersham kit) and expressed per milligram of protein in the sample. Cyclic AMP production was significantly elevated in the Alzheimer cells without L-carnitine; the presence of carnitine normalized this value in the Alzheimer cells without significantly effecting the control cells.

A derivative of L-carnitine, acetyl-caritine, is now being tested extensively in humans for the treatment of Alzheimer's disease. The utility of this approach depends on the demonstration of disease-specific abnormalities in cultured cells from the patient being studied. In the case of neurodegenerative diseases, disease-specific abnormalities might be more readily uncovered in cultured cells derived from the affected tissue, i.e. the brain, thus potentially expanding the ultility of this approach to a large number of neurodegenerative diseases. Similar cells have also been cultured in this laboratory from cerebral tissues obtained at post-mortem from neurolgically normal and diseased subjects. These cells will be useful in studies of neural cells from patients with specific diseases, including transplantation into rodents and other experimental animals to provide animal models for pharmacological testing.

Another typical use of this invention to test a neuroactive agent is to test the effect of caritine, acetyl-1-carnitine, and othr carnitine derivatives on the expression of Alzheimer-related antigens in cultured cells from Alzheimer patients and controls. Cells have been cultured by the techniques described above from autopsy samples: from the brain of a patient with Alzheimer's disease, and from the leptomeninges of another patient with Alzheimer's. These cultures were studied immunocytochemically with antibodies which react with paired helical filaments (PHF), that are a characteristic constituent of Alzheimer brain. The cultured brain and leptomeningeal cells from the Alzheimer pateints, but not the brain cells from the non-Alzheimer patient, reacted convincingly with three well characterized monoclonal antibodies to PHF (namely the $\alpha$-PHF/$\alpha$-ubiquitin antibodies 5–25 and 3-39, and the $\alpha$-PHF/$\alpha$-tau antibody Asz50). The Alzheimer, but not non-Alzheimer cultured cells also reacted with a commercial polyclonal antibody to PHF.

Thus while we have illustrated and described the preferred embodiment of our invention, it is to be understood that this invention is capable of variation and modification, and we therefore do not wish to be limited to the precise terms set forth, but desire to avail ourselves of such changes and alterations which may be made for adapting the invention to various usages and conditions. Accordingly, such changes and alterations are properly intended to be within the full range of equivalents, and therefore within the purview of the following claims.

Having thus described our invention and the manner and a process of making and using it in such full, clear, concise and exact terms so as to enable any person skilled in the art to which it pertains, or with which it is most nearly connected, to make and use the same.

We claim:

1. A cultured cell line originating from adult human brain and adult human meninges tissue, said cell line consisting of diploid cells that express neuronal markers but do not express glial markers found in cells taken from adult brain tissue.

2. The cultured cell line of claim 1 wherein said cell line is derived from autopsied adult brain tissue.

3. The cultured cell line of claim 1 wherein said cell line is derived from biopsied adult brain tissue.

4. The cultured cell line of claim 1 wherein said neuronal markers are selected from the group consisting of high neurofilaments, neuron specific enolase, medium neurofilaments and combinations thereof.

5. The cultured cell line of claim 1 wherein said meninges tissue is leptomeningeal tissue.

* * * * *